US010130652B2

(12) United States Patent
Giori et al.

(10) Patent No.: US 10,130,652 B2
(45) Date of Patent: Nov. 20, 2018

(54) ANTI-INFLAMMATORY COMPOSITIONS

(75) Inventors: Andrea Giori, Milan (IT); Sabrina Arpini, Milan (IT); Stefano Togni, Milan (IT)

(73) Assignee: INDENA S.P.A., Milan (IT)

( * ) Notice: Subject to any disclaimer, the term of this patent is extended or adjusted under 35 U.S.C. 154(b) by 814 days.

(21) Appl. No.: 13/699,248

(22) PCT Filed: May 23, 2011

(86) PCT No.: PCT/EP2011/058334
§ 371 (c)(1),
(2), (4) Date: Jan. 23, 2013

(87) PCT Pub. No.: WO2011/147768
PCT Pub. Date: Dec. 1, 2011

(65) Prior Publication Data
US 2013/0136813 A1    May 30, 2013

(30) Foreign Application Priority Data
May 24, 2010  (IT) .............................. MI2010A0934

(51) Int. Cl.
*A61K 31/715*   (2006.01)
*A61K 8/73*     (2006.01)
*A61K 8/97*     (2017.01)
*A61K 36/28*    (2006.01)
*A61K 36/48*    (2006.01)
*A61Q 11/00*    (2006.01)
*A61Q 19/00*    (2006.01)
*A61K 36/49*    (2006.01)
*A61K 36/758*   (2006.01)

(52) U.S. Cl.
CPC .............. *A61K 31/715* (2013.01); *A61K 8/73* (2013.01); *A61K 8/97* (2013.01); *A61K 36/28* (2013.01); *A61K 36/48* (2013.01); *A61K 36/49* (2013.01); *A61K 36/758* (2013.01); *A61Q 11/00* (2013.01); *A61Q 19/00* (2013.01)

(58) Field of Classification Search
None
See application file for complete search history.

(56) References Cited

U.S. PATENT DOCUMENTS 6,056,950 A  *  5/2000  Saettone .............. A61K 9/0048
                                                424/78.04
2006/0275246 A1*  12/2006  Bombardelli .......... A61K 8/375
                                                424/74
2007/0128285 A1*  6/2007  Jin et al. ...................... 424/488

FOREIGN PATENT DOCUMENTS

CN     1528460 A   *  9/2004
EP      348215 A2  * 12/1989
FR     2 851 469         8/2004
WO     2005/063186 A1    7/2005
WO     2006/123234 A1   11/2006
WO     2009/040847 A2    4/2009

OTHER PUBLICATIONS

Endocarditis infection 2008 http://web.archive.org/web/20080616123525/http://my.clevelandclinic.org/heart/disorders/valve/sbe.aspx.*
Burgalassi et al., Development and in vitro/in vivo testing of mucoadhesive buccal patches, 1996, International J Pharmaceutics, 133: 1-7.*
Hilan et al., Evaluation of the Antibacterial Activities of Ferula Hermonis (Boiss.), 2007, Lebanese Science Journal, 8: 135-151.*
Ghelardi et al., A mucoadhesive polymer extracted from tamarind seed improves the intraocular penetration and efficacy of rufloxacin in topical treatment of experimental bacterial keratitis, Antimicrobial Agents and Chemotherapy, 2004, 48(9), 3396-3401.*
Anonymous: "Imli-Tamarind-Tamarindus indica-Flora-Trees-Haryana Online—India," Jun. 11, 2009, pp. 1-3, retrieved from the Internet: http://www.haryana-online.com/Flora/imli.htm, retrieved on Jan. 25, 2011, (XP002618788).
Agrawal, et al., "Effect of Piper Longum Linn, Zingiber *Officianalis linn* and *ferula* Species on Gastric Ulceration and Secretion in Rats," Indian Journal of Experimental Biology, vol. 38, No. 10, pp. 994-998, Oct. 2000 (XP009001799).
Appendino, et al., "A meroterpenoid NF-kB inhibitor and drimane sesquiterpenoids from asafetida," Journal of Natural Products, vol. 39, No. 7, pp. 1101-1104, 2006, (XP018020846).
Burgalassi, et al., "Effect of xyloglucan (tamarind seed polysaccharide) on conjunctival cell adhesion to laminin and on corneal epithelium wound healing," European Journal of Ophthalmology, vol. 10, No. 1, pp. 71-76, Jan. 2000 (XP009143782).
Database WPI, Week 200704, Thomson Scientific, App. No. JP 2007-029585 & JP 2006-325447, Dec. 2006 (XP002618789).
Database GNPD (Online) Mintel, Anonymous: "Desert Bloom Ultrabalm", retrieved from www.gnpd.com, Database Accession No. 1054545, Jan. 2009 (XP002618790).
Database GNPD (Online) Mintel, Anonymous: "Maximum Moisture Day Cream", retrieved from www.gnpd.com, Dabatase Accession No. 911809, May 2008 (XP002618791).
Database GNPD (Online) Mintel, Anonymous: "Acne Spot Tx", retrieved from www.gnpd.com, Database Accession No. 850241, Feb. 2008 (XP002618792).
Database WPI, Week 199646, Thomson Scientific, App. No. JP 1996-461243 & JP 8-231347, Sep. 1996 (XP002618798).
Ghelardi, et al., "A mucoadhesive polymer extracted from tamarind seed improves the intraocular penetration and efficacy of rufloxacin in topical treatment of experimental bacterial keratitis", Antimicrobial Agents and Chemotherapy, vol. 48, No. 9, pp. 3396-3401, Sep. 2004 (XP002618794).

(Continued)

Primary Examiner — Terry A McKelvey
Assistant Examiner — Catheryne Chen
(74) Attorney, Agent, or Firm — Silvia Salvadori, P.C.; Silvia Salvadori

(57) ABSTRACT

The present invention relates to the use as an anti-inflammatory of tamarind seed polysaccharide (TSP) and to anti-inflammatory compositions which contain it as active ingredient. Anti-inflammatory compositions containing TSP are particularly useful for topical administration in the treatment of inflammatory diseases of the skin and mucosa.

9 Claims, No Drawings

(56) References Cited

OTHER PUBLICATIONS

Lima, et al. "Anti-inflammatory and analgesic activities of the ethanolic extracts from *Zanthoxylum riedelianum* (Rutaceae) leaves and stem bark," Journal of Pharmacy and Pharmacology, vol. 59, No. 8, pp. 1151-1158, Aug. 2007 (XP55009222).
Marchetti, et al., "Inhibition of Herpes Simplex Virus Infection by Negatively Charged and Neutral Carbohydrate Polymers," Journal of Chemotheray, vol. 7, No. 2, pp. 90-96, 1995 (XP002618796).
Mastromarino, et al. "Antiviral activity of natural and semisynthetic polysaccharides on the early steps of rubella virus infection," Journal of Antimicrobial Chemotherapy, vol. 39, No. 3, pp. 339-345, Mar. 1997 (XP002618797).
Petronio, et al., "In vitro Effect of Natural and Semi-Synthetic Carbohydrate Polymers on Chlamydia Trachomatis Infection", Chemotherapy, vol. 43, pp. 211-217, Jan. 1997 (XP000980521).
Pietropaolo, et al., "Effect of natural and semisynthetic polymers on rabies virus infection in CER cells," Research in Virology, vol. 144, pp. 151-158, Jan. 1993 (XP022352664).
Sala, et al., "Anti-inflammatory and antioxidant properties of Helichrysum italicum," Journal of Pharmacy and Pharmacology, vol. 54, No. 3, pp. 365-371, Mar. 2002 (XP008025203).
Sinibaldi, et al., "Effect of Biological and Synthetic Polymers on BK Virus Infectivity and Hemagglutination", Journal of Chemotherapy, vol. 4, No. 1, pp. 16-22, 1992, (XP009143764).
Valencia, et al., "Antinociceptive, anti-inflammatory and antipyretic effects of lapidin, a bicyclic sesquiterpene," Database Biosis (Online) Biosciences Information Service, Database Accession No. PREV199598053519, vol. 60, No. 5, pp. 395-399, 1994 (XP002661020).
Author Ziya Al-Din Abdullah Ibn Al-Baitar Title of publication—Al-Jaam'e-li-Mufradaat-al-Advia-wal-Aghzia vol. I Page(s) being submitted—05 (p. 04-08) ( Ref.p. No.of publication:141 ) Publication Date—1874 AD Publisher—Matba Amra Cairo Place of Publication—Egypt, India.†
Author Mohammad Akmal Khan Title of publication—Qaraabaadeen Azam wa Akmal (20th Century AD) Page(s) being submitted—04 (p. 9-12) ( Ref.p. No.of publication:688 ) Publication Date—1909 AD Publisher—Matba Siddiqi, Delhi / Matba Mustafai Place of Publication—Delhi, India.†
Author Ziya Al-Din Abdullah Ibn Al-Baitar Title of publication—Al-Jaam'e-li-Mufradaat-al-Advia-wal-Aghzia vol. I Page(s) being submitted—06 (p. 13-18) ( Ref.p. No.of publication: 110-111 ) Publication Date—1874 AD Publisher—Matba Amra Cairo Place of Publication—Egypt, India.†

\* cited by examiner
† cited by third party

ANTI-INFLAMMATORY COMPOSITIONS

This application is a U.S. national stage of PCT/EP2011/058334 filed on May 23, 2011, which claims priority to and the benefit of Italian Application No. MI2010A000934, filed on May 24, 2010, the contents of which are incorporated herein by reference.

TECHNICAL FIELD OF THE INVENTION

The present invention relates to the use of tamarind seed polysaccharide as an anti-inflammatory and to anti-inflammatory compositions which contain it as active ingredient.

BACKGROUND OF THE INVENTION

Tamarind seed polysaccharide (TSP) is a natural polysaccharide polymer obtained from the seeds of *Tamarindus indica*, an evergreen plant which can reach a height of 15 metres and produces fruit in the form of pods. It is very common in India, Africa and throughout the Far East, where it is mainly grown as a food. The fruit contains large seeds with a high percentage of polysaccharides, which have the function of accumulating and preserving vital energy-giving substances. Tamarind seeds, which were originally considered as waste products, have subsequently found. different applications after grinding to obtain a farinaceous product (known as tamarind gum or tamarind nut powder). The most important of these applications is in the textile industry and the paper industry, where tamarind gum is used as a sizing and gluing agent, and in the food industry where, like other polysaccharides, it is used as a thickener, gelling agent, stabiliser and binder in various products. Raw tamarind gum is a commercially available product containing from 65% to 73% by weight of polysaccharide, from 15% to 23% by weight of protein material, from 3% to 8% by weight of fats and oils, and from 2% to 1% by weight of ashes, together with smaller amounts of raw fibre, tannins and other impurities.

More recently, TSP has also been used in the pharmaceutical field as active ingredient in tear substitutes (WO2009/044423), as a carrier for slow-release ophthalmic medicaments for topical administration (WO97/28787) and, more generally, as an excipient due to its mucoadhesive characteristics

SUMMARY OF THE INVENTION

The present invention refers to the use of tamarind seed polysaccharide in treatment of inflammatory diseases.

The invention also relates to an anti-inflammatory pharmaceutical and/or dermocosmetic composition comprising tamarind seed polysaccharide as active ingredient mixed with one or more acceptable excipients.

Furthermore, the invention concerns a method of treating a patient having an inflammatory disease comprising administering a therapeutically effective amount of Tamarind seed polysaccharide,

DETAILED DESCRIPTION OF THE INVENTION

We have now found that tamarind seed polysaccharide (hereinafter called TSP) has anti-inflammatory properties, especially when administered topically.

Object of the present invention is therefore the use of TSP as an anti-inflammatory and, in particular, the use of TSP as an anti-inflammatory for topical administration.

A further object of the present invention is an anti-inflammatory pharmaceutical and/or dermocosmetic composition comprising TSP mixed with one or more acceptable excipients and, more particularly, an anti-inflammatory pharmaceutical and/or dermocosmetic composition for topical administration comprising TSP mixed with one or more acceptable excipients.

TSP can be used, as an anti-inflammatory according to the present invention, alone or in combination with other active ingredients.

A further object of the present invention is therefore the use of TSP as an anti-inflammatory in combination with one or more active ingredients and, more particularly, the use of TSP as an anti-inflammatory for topical administration in combination with one or more active ingredients.

Anti-inflammatory pharmaceutical and/or dermocosmetic compositions and, more particularly, anti-inflammatory pharmaceutical and/or dermocosmetic compositions for topical administration, comprising TSP in combination with one or more active ingredients mixed with one or more acceptable excipients, also form the object of the present invention.

According to the invention, "TSP" means a polysaccharide-enriched fraction obtained from tamarind gum commercially available, for example from Dainippon Sumitomo Pharma Ltd. under the Glyloid® trademark or from Indena SpA under the Xilogel® trademark.

The active ingredients which can be used in combination with TSP are, for example, antimicrobial agents, anti-inflammatory agents, analgesic agents, wound-healing agents.

The preferred antimicrobial agents are antibiotics such as clindamycin, erythromycin, benzylpenicillin, tetracycline, chloramphenicol, vancomycin and linezolid.

Anti-inflammatory agents include steroidal anti-inflammatory drugs, such as cortisone, and non-steroidal anti-inflammatory drugs, such as acetylsalicylic acid and ibuprofen, which have analgesic activity.

Wound-healing agents may be of natural or synthetic origin.

Particularly preferred is the combination of TSP with other extracts of plant origin, especially extracts of plant origin which possess antimicrobial and/or anti-inflammatory and/or analgesic and/or wound-healing properties.

The use of TSP in combination with other extracts of plant origin can have a synergic effect on anti-inflammatory activity.

Preferred examples of extracts of plant origin which may be used in combination with TSP are extracts of *Helichrysum italicum, Ferula* spp., *Aesculus hippocastanum* and *Zanthoxylum bungeanum*.

The extracts of *Helichrysum italicum, Ferula* spp. and *Aesculus hippocastanum* are known individually for their anti-inflammatory action.

The active ingredients in *Helichrysum italicum* extract are contained in the aerial parts of the plant, which contains non-flavonoid prenylated polyphenols. The extracts of *Helichrysum italicum* are known and can he prepared by conventional methods.

The active ingredients of *Ferula* spp. extract are contained in the whole plant, which contains ferutinin. The extracts of *Ferula* spp. are known and can be prepared by conventional methods.

The active ingredients of *Aesculus hippocastanum* extract are contained in the seed of the plant and in the bark, which contains proanthocyanidin A2 (PA2).

The extracts of *Aesculus hippocastanum* are known and can be prepared by known methods.

The active ingredients in *Zanthoxylum bungeanum* extract are contained in the pericarp, which contains alkamides. The extracts of *Zanthoxylum bungeanum* are known and can be prepared by conventional methods.

For use as an anti-inflammatory according to the present invention, TSP is formulated in suitable pharmaceutical and/or dermocosmetic compositions, preferably in topical pharmaceutical and/or dermocosmetic compositions. The topical pharmaceutical and/or dermocosmetic compositions according to the invention comprise TSP mixed with one or more suitable excipients and may be, for example, in the form of cream, ointment, gel, gum, toothpaste, mouthwash or shampoo.

TSP may generally be used in quantities of between 0.1% and 5% by weight, preferably between 0.1% and 2% by weight, and even more preferably between 0.2% and 1% by weight.

The other active ingredients optionally present in combination with TSP are used in suitable effective quantities. In the case of other extracts of plant origin used in combination with TSP, their quantity may generally be between 0.1% and 5% by weight, preferably between 0.1% and 2% by weight, and even more preferably between 0.2% and 1% by weight.

Examples of suitable excipients that may be used in the compositions according to the invention are solvents, diluents, gliding agents, preservatives, gums, sweeteners, coating agents, binders, disintegrating agents, lubricants, suspending agents, dispersing agents, colorants, flavouring agents, non-stick agents, surfactants, plasticisers, emulsifiers, chelating agents and emollients.

The solvent preferably used is water, but alcohols or other organic solvents may also be used, possibly mixed with water.

The choice of excipients is part of the normal knowledge of one skilled in the art, and will mainly depend on the pharmaceutical and/or dermocosmetic form chosen.

For example, a cream can be prepared by incorporating TSP in a topical carrier consisting of liquid paraffin, dispersed in an aqueous medium by means of lubricants. An ointment can be prepared by mixing TSP with a topical carrier such as mineral oil or wax. A gel can be prepared by mixing TSP with a topical carrier containing a gelling agent The pharmaceutical and/or dermocosmetic composition according to the invention may also be a, woven or non-woven, material coated and/or impregnated with a mixture of TSP with a suitable carrier or a matrix in which TSP is dispersed so that it comes into contact with the skin for transdermal administration. Specific examples are sticking plasters, gauze, towelettes, etc.

The choice of type of pharmaceutical and/or dermocosmetic form will depend mainly on the area to be treated and is part of the normal knowledge of one skilled in the art. For example, a gum or mouthwash may be more suitable to treat the oral cavity, whereas a cream, ointment, lotion or towelettes may be suitable for the skin of the face.

The treatment with TSP according to the present invention is effective in stimulating the anti-inflammatory response, especially when administered topically to the skin and to the mucosa.

The compositions according to the invention are therefore useful to treat any disorder of the skin or mucosa associated with an inflammatory state.

The term "skin" is used according to the present invention in its conventional meaning, namely an external organ including the epithelial tissue. The term "mucosa" is also used with its usual meaning, which relates to all the mucosal barriers in the body, such as the gastrointestinal, pulmonary, sublingual, buccal, rectal, vaginal, nasal, urethral and ocular harriers.

The compositions to which this invention relates are preferably applied by topical administration directly to the inflamed area of the skin or mucosa and/or to the surrounding area.

Numerous disorders of the skin and mucosa associated with inflammatory states are known. For example, one disorder of the skin or mucosa which can be effectively treated or prevented by applying a composition according to the invention is dermatitis.

Dermatitis is a surface inflammation of the skin characterised by the formation of blisters, erythema, oedema, exudative lesions, desquamative lesions, scab-forming lesions and intense itching. Dermatitis can be the contact, atopic or seborrhoeic type. The main treatment consists of removing the trigger, generally an irritant substance or an allergen, but that is not always possible.

A particular form of dermatitis is psoriasis, a chronic hyperproliferative inflammatory skin disease that affects approximately 1-2% of the population. Every year about 150,000 new cases of psoriasis are recorded, and approximately 400 deaths are caused by this disease. The impact of psoriasis on the patients' life is not limited to its effect on their physical appearance, but also affects their physical capacity and longevity. The most common type of psoriasis is chronic plaque psoriasis, generally a chronic condition with periods of remission and flares, characterised by erythematous desquamative plaques most frequently located on the scalp or on the extensor surfaces of the elbows and knees.

The treatment of dermatitis is generally based on corticosteroids, which present considerable side effects such as reduced immune response which leads to secondary bacterial infections, especially those caused by fungi or Candida. Moreover, this treatment requires frequent periods of suspension, and cannot he used during the acute exudative stage of the disease.

Alternatively, psoriasis can be treated by topical administration of dithranol, vitamin D3 analogues or tazarotene. These active ingredients present various side effects, such as irritation, toxicity and carcinogenicity. Phototherapy with UVA or UVB radiation can also be used to treat psoriasis, especially in patients who fail to respond to topical treatment. However, phototherapy is not devoid of side effects, such as the risk of erythema, blistering and premature aging of the skin in the case of UVB radiation, or nausea, erythema, headache, skin pain, actinic keratosis, premature aging of the skin, irregular pigmentation and squamous-cell carcinoma in the case of UVA radiation.

The compositions according to the invention allow all types of dermatitis to be treated effectively.

Even inflammations of the mucosa, especially the oral, rectal and vaginal mucosa, can be treated with the compositions according to the invention.

In particular, TSP can be used for topical treatment of inflammations of the oral mucosa such as mucositis and stomatitis.

The terms mucositis and stomatitis are often used interchangeably, although the two disorders can present some differences.

Mucositis is a toxic inflammatory reaction which affects the gastrointestinal tract and can be caused by exposure to chemotherapy agents or ionising radiation. Mucositis is generally manifested as an erythematous lesion similar to a burn or as a random ulcerative lesion from focal to diffuse.

Stomatitis is an inflammatory reaction that affects the oral mucosa, with or without ulceration, which can be caused or intensified by pharmacological. treatments, especially chemotherapy, or by radiotherapy.

The degree of stomatitis can range from mild to severe and the patient with severe stomatitis may be unable to eat or drink or take medicinal products by mouth.

Many women suffer from mouth ulcers at certain stages of the menstrual cycle and at the same time present the same type of ulcers in the genital tract, especially the vulva and vagina. They are sometimes very severe and can cause urine retention and require strong analgesics and sedatives.

The most serious form is known as Behçet's Syndrome.

According to the invention, the more general term of mucositis will also be used to indicate stomatitis, Erythematous mucositis may appear as early as three days after exposure to chemotherapy or radiotherapy, but more commonly appears after 5-7 days, The progress to ulcerative mucositis takes place within 7 days of the start of chemotherapy and can sometimes become so severe as to require discontinuance of the pharmacological treatment. Mucositis can involve the mouth and the oropharyngeal tract as well as the gastrointestinal tract from mouth to anus. In the present context, unless otherwise specified, reference is made to mucositis which relates to the more easily accessible regions such as the mouth, pharynx, oesophagus and rectum.

As a high percentage (30-40%) of patients who receive chemotherapy develop mucositis of varying degrees of severity, there is a particular need for an effective, convenient treatment, No effective treatment is currently available and attempts to solve the problem involve the use of analgesics, antiseptics and oral hygiene measures or attenuation of the symptoms.

Moreover, the problem is not limited to cancer patients, because mucositis frequently also occurs in patients with HIV, especially when associated with Kaposi's sarcoma, in patients suffering from non-Hodgkin's lymphoma, in debilitated elderly patients and in patients receiving treatments with BRMs (Biological Response Modifiers) such as interleukin-2, interferons, lymphocytes activated by lymphokines and the like.

The following examples are provided to further illustrate the present invention.

EXAMPLES

Example 1

Cream for Topical Use

| | |
|---|---|
| TSP (tamarind seed polysaccharide) | 0.400% (w/w) |
| Water | 75.150% (w/w) |
| Montanov 202 | 5.000% (w/w) |
| Lanol 99 | 10.000% (w/w) |
| Sepilift DPHP | 1.000% (w/w) |
| Monoi Butter | 2.000% (w/w) |
| Sepifeel One | 1.000% (w/w) |
| Aquaxyl | 3.000% (w/w) |
| Panthenol | 1.200% (w/w) |
| Tocopheryl acetate | 0.600% (w/w) |
| Sepicide HB | 0.300% (w/w) |
| Perfume | 0.250% (w/w) |
| Sodium hydroxide (30% sol.) | 0.100% (w/w) |
| Total | 100.000% (w/w) |

Example 2

Oral Paste

| | |
|---|---|
| TSP (tamarind seed polysaccharide) | 0.300% (w/w) |
| *Zanthoxylum bungeanum* extract | 0.300% (w/w) |
| Sorbitol | 50.000% (w/w) |
| Distilled water | 35.040% (w/w) |
| Hydrated silica | 8.000% (w/w) |
| Carboxymethylcellulose | 5.000% (w/w) |
| Potassium sorbate | 0.300% (w/w) |
| Sodium benzoate | 0.300% (w/w) |
| PEG-40 hydrogenated castor oil | 0.160% (w/w) |
| Sodium saccharine | 0.100% (w/w) |
| Flavouring | 0.500% (w/w) |
| Total | 100.000% (w/w) |

Example 3

Vaginal Cream

| | |
|---|---|
| TSP (tamarind seed polysaccharide) | 0.200% (w/w) |
| *Ferula* spp. extract | 0.200% (w/w) |
| Distilled water | 73.300% (w/w) |
| Liquid paraffin | 15.000% (w/w) |
| Cetearyl alcohol - PEG-20 stearate | 9.000% (w/w) |
| Dimethicone | 1.000% (w/w) |
| Phenoxyethanol | 0.500% (w/w) |
| Imidazolidinyl urea | 0.300% (w/w) |
| Propylparaben | 0.150% (w/w) |
| Methylparaben | 0.150% (w/w) |
| Sodium EDTA | 0.100% (w/w) |
| Lactic acid | 0.100% (w/w) |
| Total | 100.000% (w/w) |

Example 4

Myeloperoxidase Expression in Skin PMNs

Tamarind Seed Polysaccharide (either alone and in combination with standardized botanical extracts) was tested for its ability to reduce inflammation cellular response through the measurement of the inhibition of myeloperoxidase (MPO) activity in polymorphonuclear neutrophils (PMNs). Inflammation, in particular during the acute phase, causes the migration of PMNs towards the inflammation site by chemotaxis. It is also known that the degree of MPO activity is directly proportional to the number of PMNs present in the tissue and to the inflammatory response. Thus, a reduction of the number of PMNs corresponds to a reduction in the activity of myeloperoxidase and it can he then concluded that the cellular response to inflammation is reduced accordingly.

Human skin PMNs were cultivated in bacteriological Petri dishes with 100 mm diameter. Cell culture medium was RPMI-1640 supplemented with Penicillin (100 U/ml), Streptomycin (100 mcg/ml), L-glutamin (2 mM) and 10% heat-inactivated and filtered FCS (Foetal Calf Serum). PMNs were then stimulated with the addition of LPS (lipopolysaccharides) to the cultivation media.

Different standardized botanical extracts (at 0.2% concentration in the medium), either alone or in combination with Tamarind Seed Polysaccharide (at 0.2% concentration in the medium), were added to the Petri dishes. Dexamethasone (known to be a strong inhibitor of inflammatory responses and of MPO activity) was used at 0.1% as a positive reference compound. The details are reported in Table 1.

TABLE 1

| Products | Concentration |
| --- | --- |
| Basal value (after stimulation with LPS) | — |
| Positive reference (Dexamethasone) | 0.1% |
| Tamarind Seed Polysaccharide (TSP) | 0.2% |
| *Helichrysum italicum* extract (HIE) | 0.2% |
| HIE + TSP | 0.2% + 0.2% |
| *Ferula hermonis* extract (FHE) | 0.2% |
| FHE + TSP | 0.2% + 0.2% |
| *Zanthoxylum alatum* (ZA) | 0.2% |
| ZA + TSP | 0.2% + 0.2% |

After 6 hours of incubation, the overall inhibition of myeloperoxidase (MPO) activity was quantified in the PMNs cell supernatants using an enzyme immunoassay kit (ELISA). Results are reported in Table 2.

TABLE 2

| Tested products | MPO Inhibition of Expression (Δ % vs. basal) |
| --- | --- |
| Basal value (after stimulation with LPS) | — |
| Positive reference (Dexamethasone) | −30%* |
| Tamarind Seed Polysaccharide (TSP) | −40%* |
| *Helichrysum italicum* extract (HIE) | −20%* |
| HIE + TSP | −95%** |
| *Ferula hermonis* extract (FHE) | −15%* |
| FHE + TSP | −93%** |
| *Zanthoxylum alatum* extract (ZAE) | −30%* |
| ZAE + TSP | −88%** |

*p < 0.01 vs. control
**p < 0.01 vs. positive reference (Dexamethasone)

The invention claimed is:

1. A method of treating inflammatory diseases comprising:
   administering between 0.2% and 1% (w/w) of Tamarind seed polysaccharide in combination with between 0.2% and 1% (w/w) of an extract of *Ferula hermonis* in the total composition to a patient in need thereof,
   wherein said inflammatory diseases comprise dermatitis, mucositis or stomatits.

2. The method of claim 1 for topical administration.

3. An anti-inflammatory pharmaceutical and/or dermocosmetic composition comprising between 0.2% and 1% (w/w) of tamarind seed polysaccharide in combination with between 0.2% and 1% (w/w) of an extract of *Ferula hermonis* in the total composition as active ingredients mixed with one or more acceptable excipients.

4. A composition according to claim 3, for topical administration.

5. A composition according to claim 3, in the form of cream, ointment, gel, lotion, gum, toothpaste, mouthwash or shampoo.

6. A composition according to claim 3, comprising at least a further active ingredient selected from the group consisting of antimicrobial agents, anti-inflammatory agents, analgesic agents and wound-healing agents.

7. A composition according to claim 3, further comprising between 0.2% and 1% (w/w) an extract of *Aesculus hippocastanum* in the total composition.

8. A method of treating a patient having an inflammatory disease comprising administering between 0.2% and 1% (w/w) of Tamarind see polysaccharide in combination with between 0.2% and 1% (w/w) of an extract of *Ferula hermonis* in the total composition, wherein said inflammatory disease comprises dermatitis, mucositis or stomatitis.

9. An anti-inflammatory pharmaceutical and/or dermocosmetic composition comprising about 0.2% (w/w) tamarind seed polysaccharide in combination with about 0.2% (w/w) of an extract of *Ferula hermonis* in the total composition as active ingredients mixed with one or more acceptable excipients.

* * * * *